US007942865B2

(12) United States Patent
Johnson

(10) Patent No.: US 7,942,865 B2
(45) Date of Patent: May 17, 2011

(54) CORONARY SINUS LEAD DELIVERY CATHETER

(75) Inventor: Eric T. Johnson, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/497,760

(22) Filed: Jul. 6, 2009

(65) Prior Publication Data

US 2009/0270836 A1 Oct. 29, 2009

Related U.S. Application Data

(63) Continuation of application No. 10/916,353, filed on Aug. 11, 2004, now Pat. No. 7,556,625.

(51) Int. Cl.
*A61M 25/16* (2006.01)

(52) U.S. Cl. ........................................ 604/530; 604/523

(58) Field of Classification Search .... 604/95.01–95.05, 604/500, 523–532
See application file for complete search history.

(56) References Cited

U.S. PATENT DOCUMENTS 5,203,776 A 4/1993 Durfee
5,322,509 A * 6/1994 Rickerd ........................ 604/532
5,423,772 A 6/1995 Lurie et al.
5,423,773 A 6/1995 Jimenez
5,549,581 A 8/1996 Lurie et al.
5,603,704 A * 2/1997 Brin et al. ..................... 604/532
5,643,231 A 7/1997 Lurie et al.
5,722,963 A 3/1998 Lurie et al.
5,846,229 A * 12/1998 Berg ............................ 604/528
5,873,842 A 2/1999 Brennen et al.
5,876,385 A * 3/1999 Ikari et al. ..................... 604/523
5,879,499 A * 3/1999 Corvi ............................ 156/175
5,971,974 A * 10/1999 Keisz ............................ 604/523
5,984,909 A * 11/1999 Lurie et al. .................... 604/524
6,001,085 A * 12/1999 Lurie et al. .................... 604/524
6,126,649 A 10/2000 Van Tassell et al.
6,132,417 A 10/2000 Kiesz
6,277,107 B1 * 8/2001 Lurie et al. .................... 604/528
6,445,958 B1 9/2002 Machek et al.
6,458,107 B1 10/2002 Ockuly
6,558,368 B1 * 5/2003 Voda ............................ 604/532
6,610,058 B2 8/2003 Flores
6,612,999 B2 9/2003 Brennan et al.
6,638,268 B2 10/2003 Niazi
6,656,166 B2 12/2003 Lurie et al.
6,723,083 B2 4/2004 Kiemeneij
6,758,854 B1 7/2004 Butler et al.
6,823,217 B2 11/2004 Rutten et al.
2003/0028153 A1 2/2003 Brennan et al.
(Continued)

OTHER PUBLICATIONS

Pressure Products Booklet from May 2002 NASPE Conference (2 pages).

*Primary Examiner* — Nicholas D Lucchesi
*Assistant Examiner* — Gerald Landry, II
(74) *Attorney, Agent, or Firm* — Faegre & Benson LLP

(57) ABSTRACT

A guide catheter for accessing the coronary sinus ostium has a proximal portion and a distal portion formed into a preformed shape including a curved segment. The preformed shape includes a first arc, a second arc, a third arc, a fourth arc, and a generally straight terminal portion. The preformed shape is generally a J-shape, having a terminal portion generally parallel to the proximal portion, a generally closed arc or a generally open arc.

16 Claims, 8 Drawing Sheets

12
170
56
54
100
14

U.S. PATENT DOCUMENTS

2003/0040736 A1 2/2003 Stevens et al.
2003/0144657 A1 * 7/2003 Bowe et al. .................... 606/41
2003/0195525 A1 10/2003 Peterson et al.
2003/0208141 A1 * 11/2003 Worley et al. ................ 600/585
2003/0208220 A1 11/2003 Worley et al.
2004/0019359 A1 1/2004 Worley et al.
2004/0092844 A1 * 5/2004 Johnson et al. .............. 600/585
2004/0102830 A1 * 5/2004 Williams ..................... 607/125
2004/0116993 A1 * 6/2004 Clemens et al. ............. 607/122
2004/0220520 A1 11/2004 Simpson et al.

* cited by examiner

CORONARY SINUS LEAD DELIVERY CATHETER

CROSS-REFERENCE TO RELATED APPLICATIONS

This application is a continuation of U.S. patent application Ser. No. 10/916,353, titled "CORONARY SINUS LEAD DELIVERY CATHETER," filed Aug. 11, 2004, which is incorporated herein by reference in its entirety.

This application is also related to co-pending and commonly-assigned U.S. patent application Ser. No. 11/733,919, titled "CORONARY SINUS LEAD DELIVERY CATHETER," filed Apr. 11, 2007 and also to co-pending and commonly-assigned U.S. patent application Ser. No. 10/916,148, titled "RIGHT-SIDE CORONARY SINUS LEAD DELIVERY CATHETER," filed on Aug. 11, 2004, both of which are incorporated herein by reference in their entirety.

TECHNICAL FIELD

This invention relates to cardiovascular guide catheters and methods of using the catheters. More specifically, it relates to a guide catheter for locating and cannulating the coronary sinus.

BACKGROUND

Guiding catheters are instruments that allow a physician to access and cannulate vessels in a patient's heart for conducting various medical procedures, including venography and implantation of cardiac leads. Cannulating heart vessels requires navigating a small-diameter flexible guide catheter through the tortuous vasculature into a heart chamber, and then into a destination heart vessel. Once the destination heart vessel is reached, the catheter acts as a conduit for insertion of payloads, for example pacing leads, into the vessel.

Guiding catheter systems are often configured with a preshaped profile that is optimized for the intended vessel destination. One commonly accessed destination vessel for placement of cardiac pacing leads is the coronary sinus. Typically, access to the coronary sinus is gained through the left subclavian vein. The coronary sinus may also be accessed through the right subclavian vein.

There is a need for a lead delivery system and method to allow accurate and rapid lead implantation and anchoring in the coronary sinus or sub-branches of the coronary sinus.

SUMMARY

The present invention, according to one embodiment, is a guide catheter for accessing the coronary sinus. The guide catheter includes a flexible elongate shaft having a proximal portion and a distal portion having a preformed shape. The preformed shape includes a first arc having a first arc radius of from about 3.0 to about 4.0 inches, a second arc distally adjacent the first arc and having a second arc radius of from about 1.2 to about 1.8 inches, a third arc distally adjacent the second having a third arc radius of from about 2.2 to about 3.7 inches, and a fourth arc distally adjacent the third arc having a fourth arc radius of from about 1.0 to about 1.5 inches. The distal portion terminates in a generally straight terminal portion adjacent the fourth arc and having a length of from about 0.3 to about 1.9 inches. Optionally, the second arc and the third arc are combined into a single middle arc having a middle arc radius of from about 2.2 to about 3.7 inches. According to one embodiment, the preformed shape is generally a J-shape wherein the terminal portion is generally parallel to the proximal portion. According to another embodiment, the preformed shape is a generally closed arc. According to yet another embodiment, the preformed shape is a generally open arc.

The present invention, according to another embodiment, is a method of cannulating the coronary sinus. The method includes providing a flexible elongate shaft having a proximal portion and a distal portion and forming the distal portion into a preformed shape. The preformed shape includes a first arc having a first arc radius of from about 3.0 to about 4.0 inches, a second arc distally adjacent the first arc having a second arc radius of from about 1.2 to about 1.8 inches, a third arc distally adjacent the second having a third arc radius of from about 2.2 to about 3.7 inches, a fourth arc distally adjacent the third arc having a fourth arc radius of from about 1.0 to about 1.5 inches and a generally straight terminal portion distally adjacent the fourth arc and having a length of from about 0.3 to about 1.9 inches. The distal portion is inserted into an insertion vessel and the proximal portion is manipulated so as to insert the distal portion into the coronary sinus.

According to one embodiment, manipulating the distal portion includes advancing the distal portion through the superior vena cava, and into the right atrium using the superior vena cava for support, until the terminal portion crosses the tricuspid valve. The distal portion is torqued 90 degrees counterclockwise to maneuver the terminal portion into the same plane as the coronary sinus ostium. The distal portion is withdrawn back into the right atrium while torque is maintained. The terminal portion is advanced into the coronary sinus ostium while maintaining torque.

According to another embodiment, the method of cannulating the coronary sinus includes providing a guide wire and an inner catheter slidable within the shaft. The inner catheter is advanced through the guide catheter, beyond the terminal portion, and torqued to located the coronary sinus ostium. The guide wire is advanced through the inner catheter, and the guide wire and the inner catheter are alternately advanced into the coronary sinus ostium. The terminal portion is advanced over the inner catheter and into the coronary sinus ostium.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
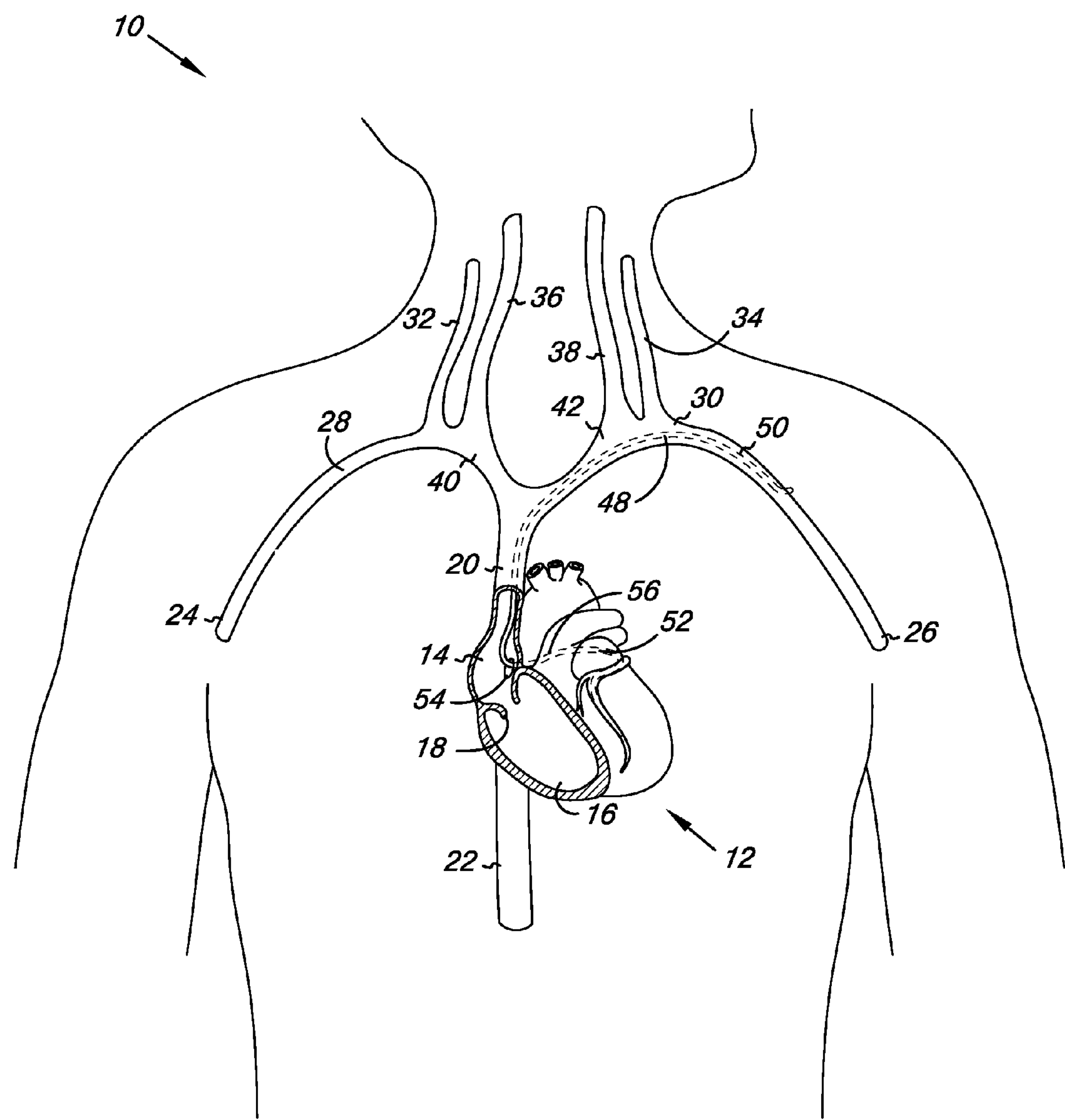
FIG. 1 is a schematic view of a catheter deployed in a heart and parts of the vascular system, according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a catheter 10 deployed in a human heart 12 according to an embodiment of the present invention. As shown in FIG. 1, the heart 12 includes a right atrium 14 and a right ventricle 16 separated by a tricuspid valve 18. During normal operation of the heart 12, deoxygenated blood is fed into the right atrium 14 through the superior vena cava 20 and the inferior vena cava 22. The major veins supplying blood to the superior vena cava 20 include the right and left axillary veins 24 and 26, which flow into the right and left subclavian veins 28 and 30. The right and left external jugular 32 and 34, along with the right and left internal jugular 36 and 38, join the right and left subclavian veins 28 and 30 to form the right and left brachiocephalic veins 40 and 42. The right and left brachiocephalic veins 40 and 42 combine to flow into the superior vena cava 20.

The catheter 10, shown in FIG. 1, includes a flexible, elongate shaft 48 extending from a proximal end 50 to a distal portion 52. As shown in FIG. 1, the catheter 10 enters the vascular system through a wall of the left subclavian vein 30, extends through the left brachiocephalic vein 42 and the superior vena cava 20, and enters the right atrium 14. As further shown, catheter 10 then enters the coronary sinus ostium 54 so that the distal portion 52 of the catheter 10 is located in the coronary sinus 56. In other embodiments of the present invention, the catheter 10 enters the vascular system through the left axillary vein 26, the left external jugular 34, the left internal jugular 38, or the left brachiocephalic vein 42. The catheter 10 may be a guide catheter for assisting with placement of a cardiac pacing lead.

Figure 2:
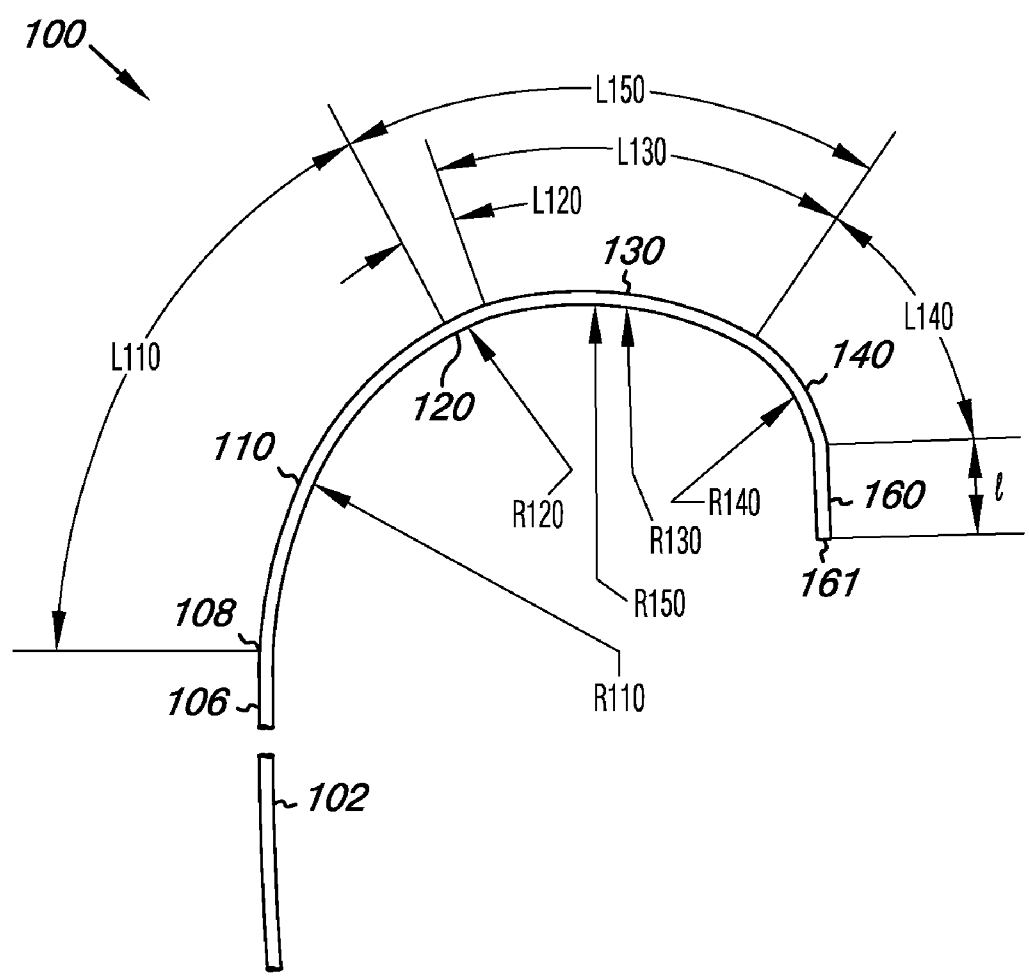
FIG. 2 is a side view of a catheter according to one embodiment of the present invention.

FIG. 2 illustrates a catheter 100 in accordance with a first embodiment of the present invention. As shown in FIG. 2, the catheter 100 has a proximal portion 102 and a distal portion 106. The proximal portion 102 is manipulated by the surgeon to advance the distal portion 106 into the patient's anatomy to access the coronary sinus 56. While the proximal portion 102 is generally straight, the distal portion 106 is advantageously pre-shaped beginning at a deflection location 108, providing an optimized geometry for locating specific vascular features (e.g., the coronary sinus 56). The pre-shaped distal portion 106 includes a series of arcs or curves.

As shown in FIG. 2, the distal portion 106 includes a first arc or catheter segment 110, which is coupled to a second arc or catheter segment 120. Extending from the distal end of the catheter segment 120 is a third arc or catheter segment 130, which is coupled to a fourth arc or catheter segment 140. Extending from the distal end of the catheter segment 140 is a generally straight end or terminal segment 160 having a length l. Optionally, the terminal segment 160 is not present. In one embodiment, the distal portion 106 has a co-planar configuration such that the shaped curve lies in a plane. In one embodiment, the second segment 120 and third segment 130 are replaced with a combined arc or catheter segment 150, as further discussed below.

The various catheter segments are shaped and angled relative to each other to provide an elongate curvature to the distal portion 106. To provide the overall shape, each of the catheter segments 110, 120, 130, and 140 has a specific radius and arc length. The catheter segment 110 has an arc radius R110 and an arc length L110, the catheter segment 120 has an arc radius R120 and an arc length L120, the catheter segment 130 has an arc radius R130 and an arc length L130, and the catheter segment 140 has an arc radius R140 and an arc length L140. In various embodiments, the various arc radii and arc lengths are scaled up or down to allow for different sized patient physiology. In some embodiments, the radius R120 and the radius R130 are the same or nearly the same. In this situation, the catheter segment 120 and the catheter segment 130 merge into a single, generally longer middle segment 150 having an arc radius R150 and an arc length L150.

In various embodiments, different radii and arc lengths can be used. For example, in various embodiments, the radius R110 is from about 3 inches to about 4 inches and the arc length L110 is from about 2 inches to about 4 inches; the radius R120 is from about 1.2 inches to about 1.8 inches and the arc length L120 is from about 0.1 inches to about 0.7 inches; the radius R130 is from about 2.2 inches to about 3.7 inches and the arc length L130 is from about 1.4 inches to about 3.3 inches; and the radius R140 is from about 1 inch to about 1.5 inches and the arc length L140 is from about 0.7 inches to about 2 inches. In the embodiments wherein the segments 120 and 130 are combined into a segment 150, the combined radius R150 is from about 2.2 inches to about 3.0 inches and the arc length L150 is from about 2.2 inches to about 3.0 inches. The length l of the end portion 160 is from about 0 (i.e., end portion 160 is not present) to about 1.9 inches.

According to one embodiment of the present invention, the distal portion 106 is generally J-shaped such that the terminal portion 160 is generally parallel to the proximal portion 102. According to an exemplary catheter having a J-shaped distal portion, the segment 110 is curved so as to have a radius R110 of about 3.88 inches and an arc length L110 of about 3.95 inches, the segment 120 is curved so as to have a radius R120 of about 1.41 inches an arc length L120 of about 0.4 inches, the segment 130 is curved so as to have a radius R130 of about 2.93 inches an arc length L130 of about 2.4 inches, the segment 140 is curved so as to have a radius R140 of about 1.18 inches and an arc length L140 of about 1.28 inches, and the end portion 160 has a length l of about 0.95 inches.

Table 1 below shows dimensions of radius of curvature and arc length for several exemplary embodiments of a catheter 100 according to the present invention, including examples wherein the segments 120 and 130 are combined into a single segment 150.

TABLE 1

| | R110 | L110 | R120 | L120 | R130 | L130 | R140 | L140 | I |
|---|---|---|---|---|---|---|---|---|---|
| 1 | 3.88 | 3.95 | 1.41 | 0.4 | 2.93 | 2.4 | 1.18 | 1.28 | 0.95 |
| 2 | 3.88 | 3.95 | 1.63 | 0.57 | 3.5 | 1.53 | 1.0 | 1.4 | 0.5 |

| | R110 | L110 | R150 | L150 | R140 | L140 | I |
|---|---|---|---|---|---|---|---|
| 3 | 3.88 | 3.27 | 2.47 | 2.7 | 1.33 | 1.74 | 1.41 |

Figure 3:
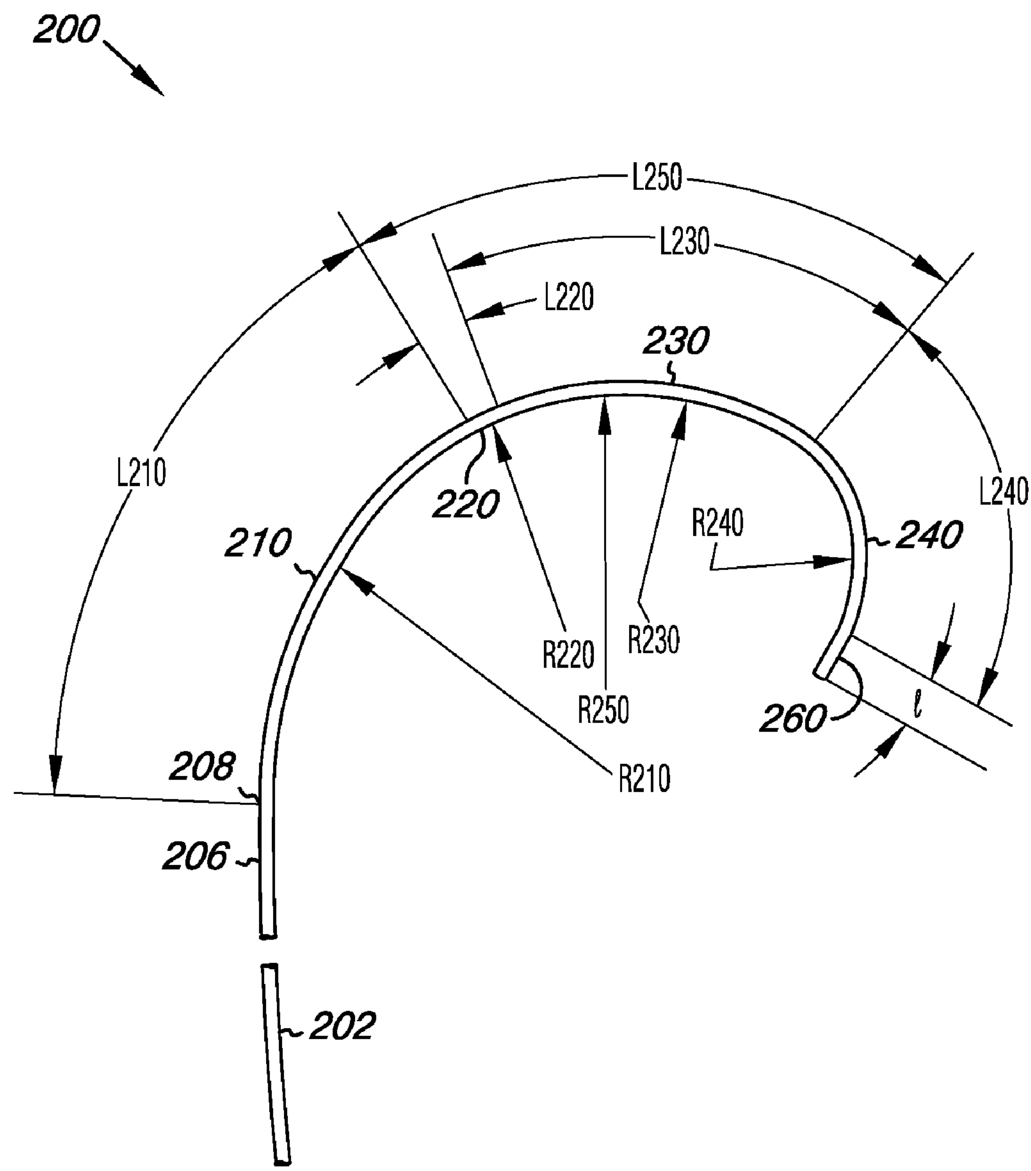
FIG. 3 is a side view of a catheter according to another embodiment of the present invention.

FIG. 3 illustrates a catheter 200 according to another embodiment of the present invention. As shown in FIG. 3, the catheter 200 has a proximal portion 202 and a distal portion 206. Again, the proximal portion 202 is adapted for manipulation by a surgeon to advance the distal portion 206 into the patient's anatomy to access the coronary sinus 56. As shown in FIG. 3, the distal portion 206 includes a first arc or catheter segment 210, which is coupled to a second arc or catheter segment 220. Extending from the distal end of the catheter segment 220 is a third arc or catheter segment 230, which is coupled to a fourth arc or catheter segment 240. Extending from the distal end of the catheter segment 240 is a generally straight end or terminal segment 260 having a length l. In this embodiment, the overall shape of the distal portion 206 is a closed arc in which the distal end 206, if extended, would intersect with the catheter proximal portion 202. In other words, the overall curvature of the distal portion 206 exceeds 180 degrees of rotation.

In this embodiment, the segment 210 is curved so as to have an arc radius R210 of from about 3.5 to about 4 inches and an arc length L210 of from about 3 to about 4 inches; the segment 220 is curved so as to have an arc radius R220 of from about 1.3 to about 1.5 inches and an arc length L220 of from about 0.1 to about 0.2 inches; the segment 230 is curved so as to have an arc radius R230 of from about 2.4 to about 2.7 inches and an arc length L230 of from about 2.8 to about 3.2 inches; the segment 240 is curved so as to have an arc radius R240 of from about 1 to about 1.5 inches and an arc length L240 of from about 1.5 to about 2.2 inches; and the end portion 260 has a length l of from about 0 to about 1 inch.

Table 2 below shows dimensions of radius of curvature and arc length for several exemplary embodiments of a catheter 200 according to the present invention, including examples wherein the segments 220 and 230 are combined into a single segment 250 having an arc radius R250 and an arc length L250.

TABLE 2

| | R210 | L210 | R220 | L220 | R230 | L230 | R240 | L240 | I |
|---|---|---|---|---|---|---|---|---|---|
| 1 | 3.88 | 3.95 | 1.41 | 0.14 | 2.54 | 3.06 | 1.27 | 1.72 | 0.4 |

| | R210 | L210 | R250 | L250 | R240 | L240 | I |
|---|---|---|---|---|---|---|---|
| 2 | 3.88 | 3.27 | 2.47 | 2.78 | 1.07 | 1.92 | 0.52 |
| 3 | 3.88 | 3.27 | 2.47 | 2.78 | 1.07 | 1.85 | 1.49 |
| 4 | 3.88 | 3.27 | 2.47 | 2.7 | 1.07 | 1.75 | 1.05 |

Figure 4:
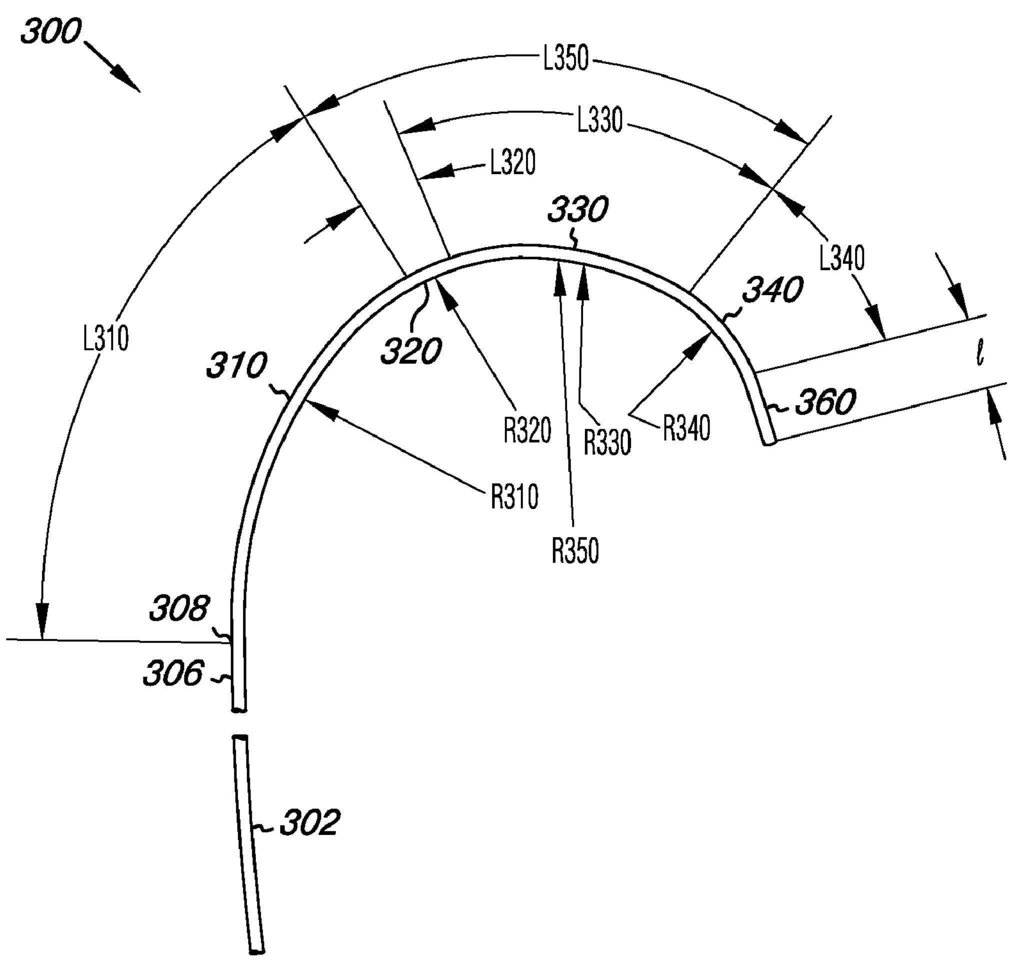
FIG. 4 is a side view of a catheter according to yet another embodiment of the present invention.

FIG. 4 illustrates a catheter 300 according to another embodiment of the present invention. The catheter 300 has a proximal portion 302 and a distal portion 306. As shown in FIG. 4, the distal portion 306 includes a first arc or catheter segment 310, which is coupled to a second arc or catheter segment 320. Extending from the distal end of the catheter segment 320 is a third arc or catheter segment 330, which is coupled to a fourth arc or catheter segment 340. Extending from the distal end of the catheter segment 340 is a generally straight end or terminal segment 360 having a length l. As further shown in FIG. 4, the overall shape of the distal portion 306 is an open arc, in which the distal end 306, if extended, would extend away from the catheter 300. In other words, the overall curvature of the distal portion 306 is less than 180 degrees of rotation.

In this embodiment, the segment 310 is curved so as to have a radius R310 of from about 3 to about 4 inches and an arc length L310 of from about 3.6 to about 4.4 inches; the segment 320 is curved so as to have a radius R320 of from about 1.2 to about 1.6 inches and an arc length L320 of from about 0.2 to about 0.4 inches; the segment 330 is curved so as to have a radius R330 of from about 2.5 to about 3.5 inches and an arc length L330 of from about 2.8 to about 3.4 inches; and the segment 340 is curved so as to have a radius R340 of from about 1 to about 1.5 inches and an arc length L340 of from about 0.8 to about 1.2 inches. The end portion 360 has a length l of from about 0 to about 1.5 inches.

Table 3 below shows dimensions of radius of curvature and arc length for several exemplary embodiments of a catheter 300 according to the present invention, including examples wherein the segments 320 and 330 are combined into a single segment 350 having a radius R350 and an arc length L350.

TABLE 3

| | R310 | L310 | R320 | L320 | R330 | L330 | R340 | L340 | I |
|---|---|---|---|---|---|---|---|---|---|
| 1 | 3.88 | 3.95 | 1.41 | 0.3 | 2.97 | 3.1 | 1.3 | 0.91 | 0.97 |

| | R310 | L310 | R350 | L350 | R340 | L340 | I |
|---|---|---|---|---|---|---|---|
| 2 | 3.05 | 2.15 | 3.27 | 2.57 | 1.35 | 1.37 | 0.91 |
| 3 | 3.88 | 3.27 | 2.47 | 2.78 | 1.07 | 0.93 | 1.81 |
| 4 | 3.88 | 3.27 | 2.47 | 2.78 | 1.07 | 0.93 | 1.3 |

Referring generally to FIG. 1, the shaft 48 of the catheter 10 may be made from any material generally known in the art, including for example PEBAX® and urethane. In one example, the catheter 10 is formed by melting PEBAX® under a shrink tube, stripping the shrink tube, installing a shape mandrel and heating it to a forming temperature. In one embodiment, a pre-shaped wire or stylet is inserted into a lumen in the mandrel to give the mandrel the desired shape. The catheter 10 is then placed over the mandrel and heated to allow it to take the desired shape. In one embodiment, for example, the catheter 10 is heated at about 280° Fahrenheit for about 20 minutes. Upon cooling the catheter 10 will retain the shape of the mandrel. An alternate construction includes a multi-layer design. In one embodiment, the shaft 48 includes a support material such as steel braiding, for example.

The distal portion 52 also includes a series of sections having different lengths. These sections are made of a thermoplastic material such as a thermo polymer having a varying durometer or degree of hardness. According to one embodiment, the hardness of the distal portion 52 softens proximally to distally, such that the distal portion 52 has a lower degree of hardness than the proximal portion 50. In one embodiment, any thermoplastic material is used to form the catheter 10.

Guide catheters are employed in a variety of applications. One exemplary application involves a method of gaining access to the coronary sinus 56. The coronary sinus access method involves inserting the catheter 100 through an incision in an appropriate access vessel. Common access vessels include the subclavian veins, the internal jugular veins, and the brachiocephalic veins.

It will be appreciated by those skilled in the art that the pre-formed shape allows the distal portion 106 to be steered by rotating the proximal portion 102. The ability to rotationally steer the distal portion 106 provides a guide catheter 100 according to the present invention useful in locating specific vascular features. In particular, the configuration of the pre-formed distal portion 106 enables the guide catheter 100 to find support from the walls of the superior vena cava 20, rather than the right atrium 14, during insertion procedures. This feature is advantageous because the size, configuration and location of the right atrium 14 tends to vary widely from patient to patient, particularly in patients having diseases of the heart. In contrast, the superior vena cava 20 tends to remain relatively constant in size and location. Thus, less time need generally be spent on locating the coronary sinus ostium 54 when utilizing the superior vena cava 20 for support than when relying on the right atrium 14. A guide catheter 100 according to the present invention thus advantageously provides a reliable and efficient tool for accessing the coronary sinus 56 via the right atrium 14.

Figure 5:
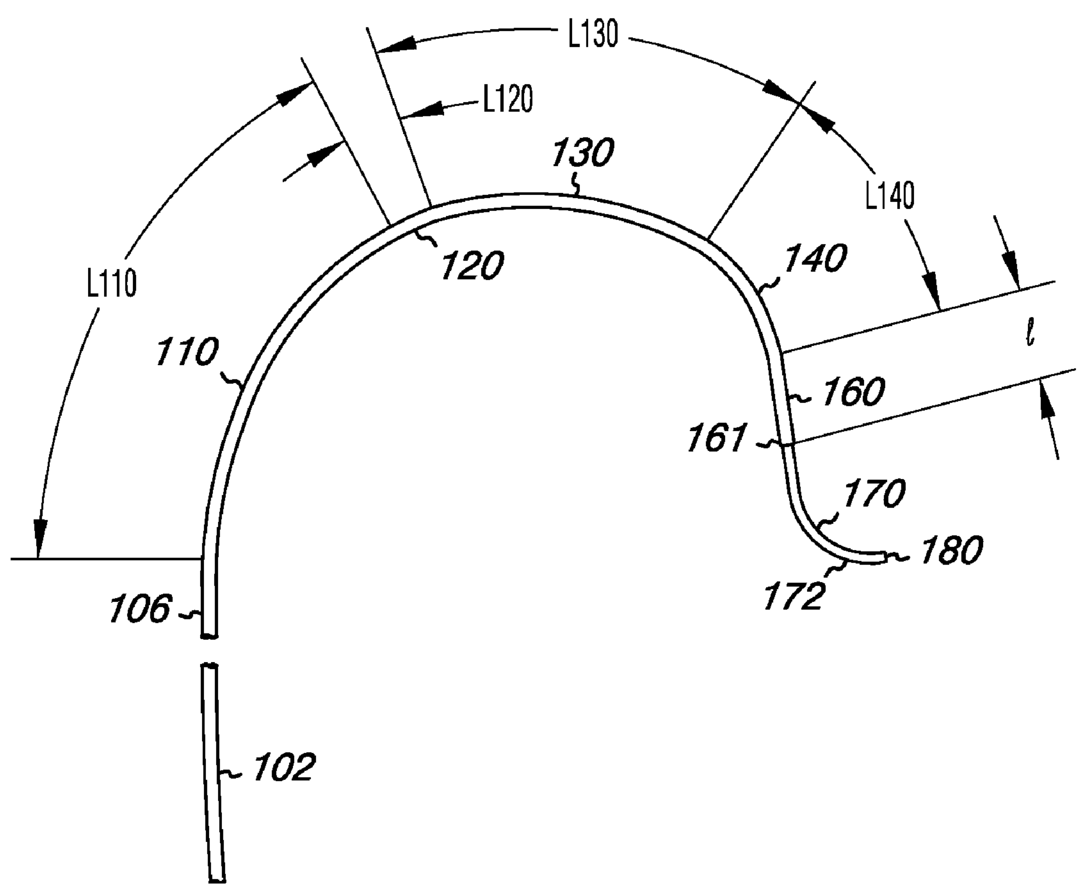
FIG. 5 is a side view of a catheter assembly according to another embodiment of the present invention.

FIG. 5 shows the guide catheter 100 of FIG. 2 assembled with an inner catheter 170. The inner catheter 170 has a preformed distal end 172, so that relative rotation and extension of the inner catheter 170 and guide catheter 100 provides the distal end 152 of the guide catheter 100 with an adjustable range of two- and three dimensional shapes. An example of this is described is U.S. Patent Publication 2003/0144657, which is hereby incorporated by reference. Furthermore, as illustrated, extension of the distal end 172 of the inner catheter 170 beyond the distal end 152 of the guide catheter shaft 148 results in a catheter assembly having a compound curvature.

Figure 6:
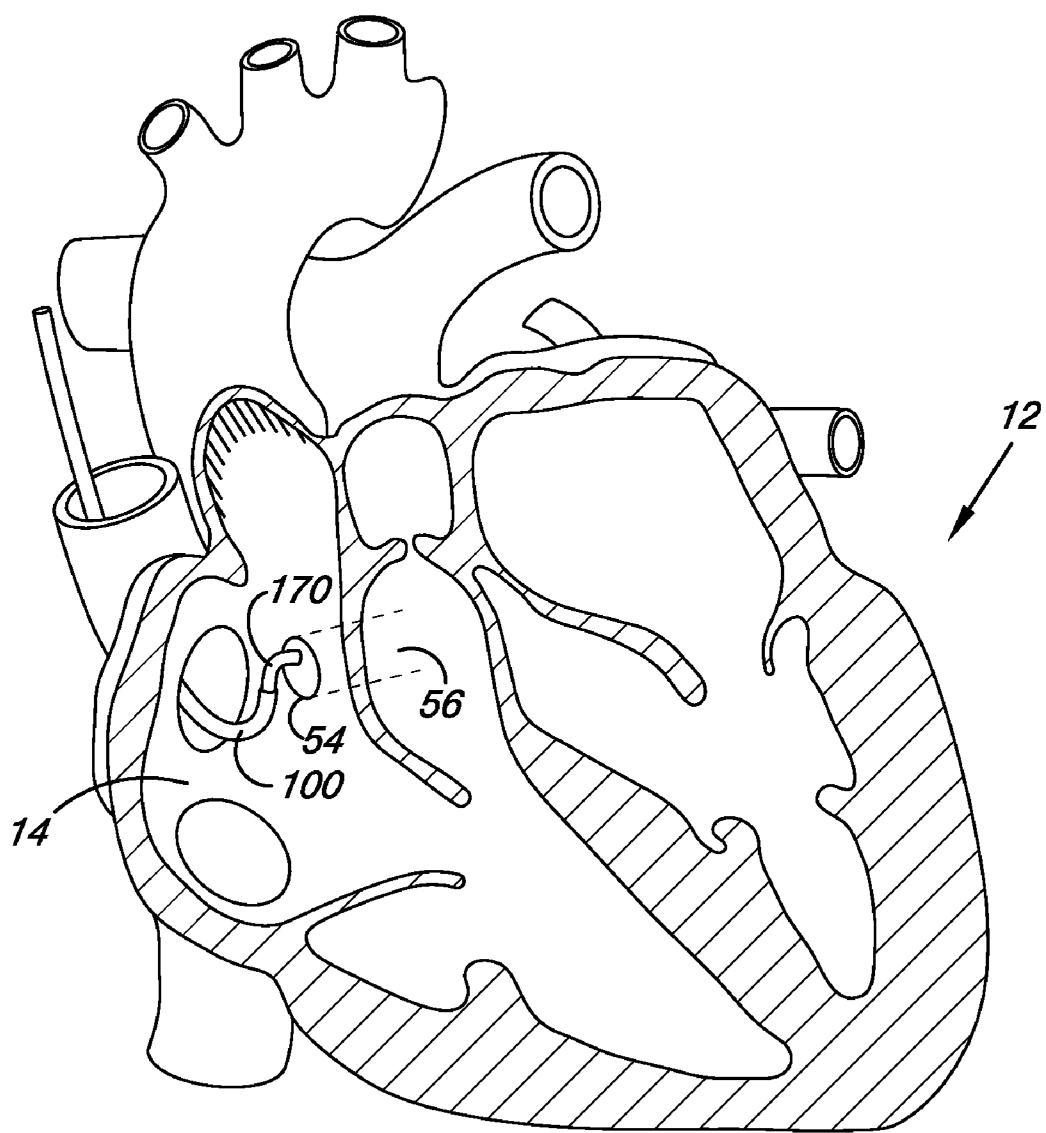
FIG. 6 is a schematic view of the catheter assembly of FIG. 5 deployed in the heart according to one embodiment of the present invention.

FIG. 6 shows the catheter assembly of FIG. 5 deployed in the heart 12. The curvature of the guide catheter 100 provides easy access through the coronary sinus ostium 54 from the right atrium 14. The inner catheter 170 is advanced through the guide catheter shaft 148 and longitudinally extended to sub-select a branch of the coronary sinus 56. The guide catheter 100 is then advanced over the inner catheter 170 into the side branch. The inner catheter 170 is removed by proximally sliding the inner catheter 170 out of the catheter 100.

Optionally, a guide wire 180 may also be employed in conjunction with a guide catheter according to the present invention (See FIG. 5). The guide wire 180 is often introduced through the access vessel into the right atrium 14. The guide catheter 100 is advanced over the guide wire 180 into the right atrium 14 through the superior vena cava 20, for example. Typically, the catheter 100 is then deployed over the guide wire 180, the guide wire 180 helping to provide support and guidance for the catheter assembly 100 as it is advanced into the right atrium 14. From the right atrium 14, the catheter 100 is used to effectively locate and cannulate the coronary sinus 56.

After the guide catheter shaft 148 is seated in the coronary sinus 56, the guide catheter shaft 148 can be used to introduce a payload into the heart 12. If the guide wire 180 or inner catheter 170 were used, they may also be removed. The payload in one exemplary embodiment is a pacing lead. Once the payload has been successful seated, the guide catheter 100 can then be removed. Assuming the payload is to remain in the heart, the guide catheter 100 is moved in a proximal direction over the payload until the guide catheter 100 is removed from the access vessel.

Figure 7:
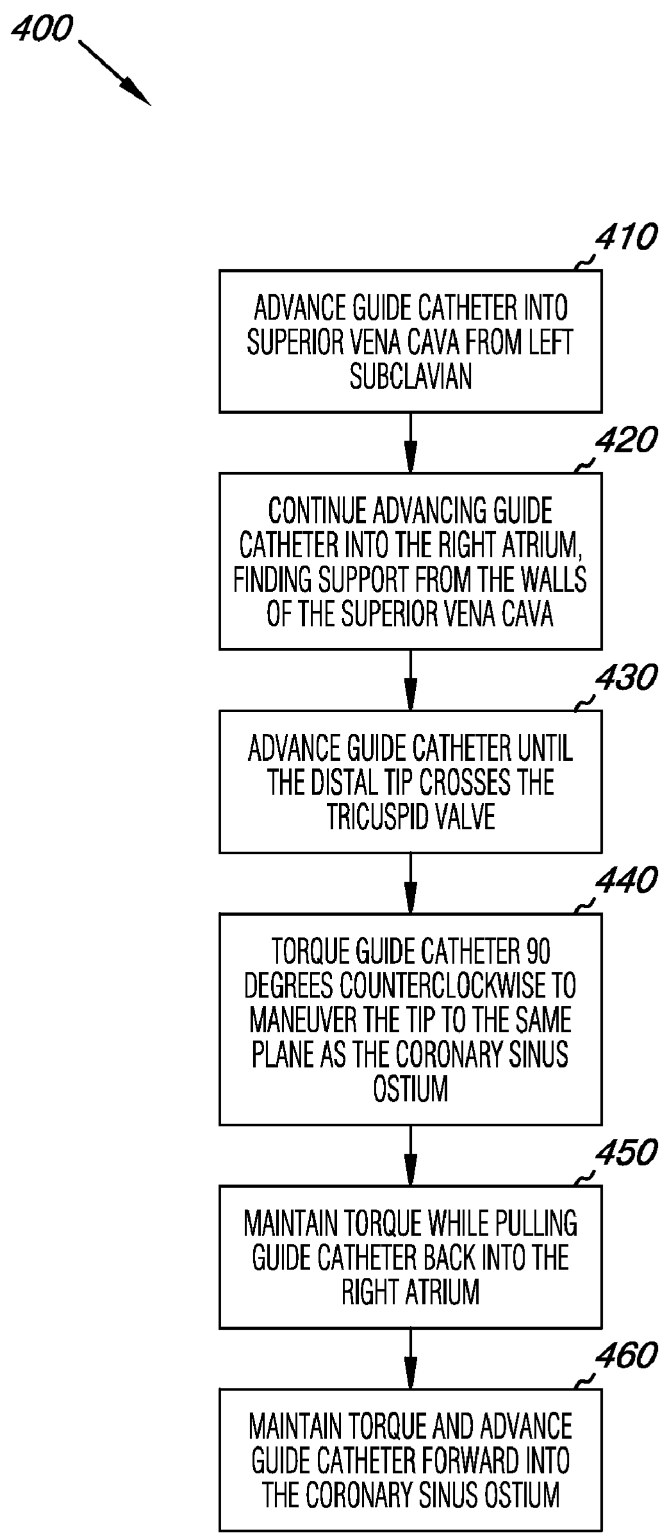
FIG. 7 is a flowchart depicting a method of accessing the coronary sinus according to one embodiment of the present invention.

FIG. 7 illustrates a method 400 of employing a guide catheter to cannulate a vessel of the heart according to one embodiment of the present invention. A guide catheter in accordance with the present invention is advanced into the superior vena cava from the left subclavian vein (block 410). The guide catheter is advanced into the right atrium, finding support from the walls of the superior vena cava (block 420). The guide catheter is advanced until the distal tip crosses the tricuspid valve (block 430). The guide catheter is torqued 90 degrees counterclockwise to maneuver the distal tip into the same plane as the coronary sinus ostium (block 440). The torque is maintained while pulling the guide catheter back into the right atrium (block 450). Finally, torque is maintained and the guide catheter is advanced forward into the coronary sinus ostium (block 460).

Figure 8:
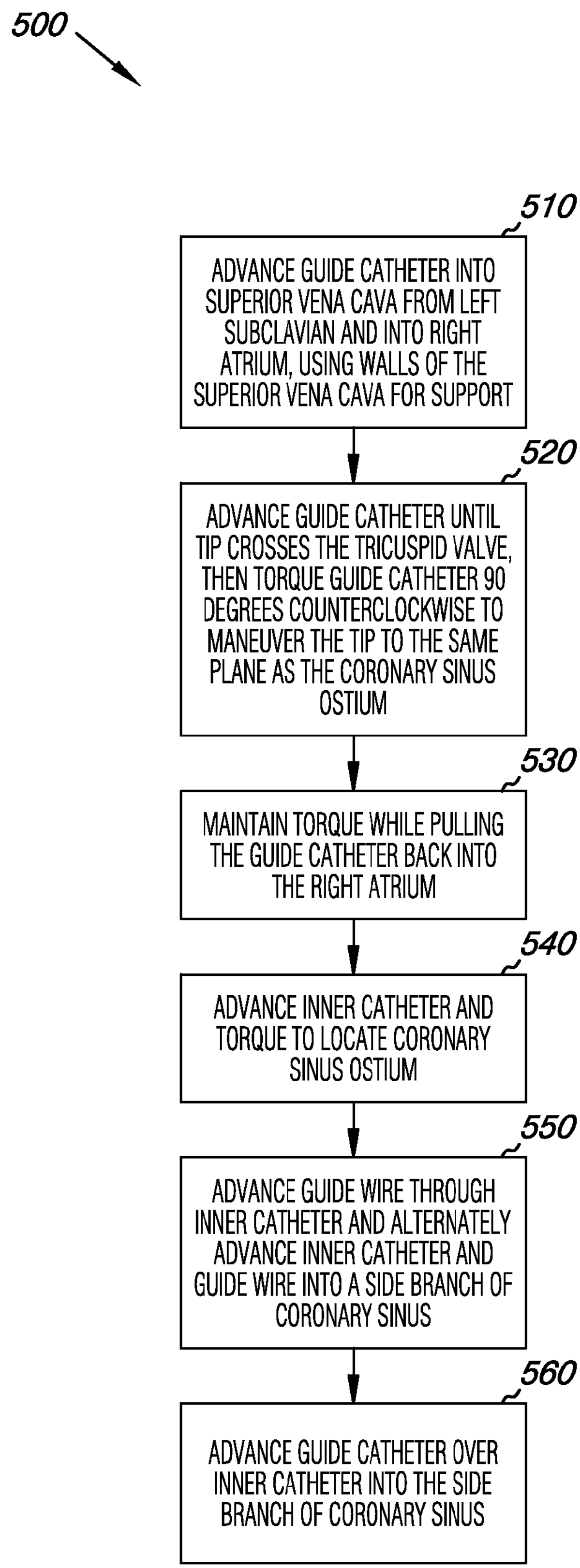
FIG. 8 is a flowchart depicting a method of accessing the coronary sinus according to another embodiment of the present invention.

FIG. 8 illustrates another method 500 of employing a guide catheter in conjunction with an inner catheter and a guide wire to cannulate a vessel of the heart according to another embodiment of the present invention. The guide catheter is advanced into the superior vena cava from the left subclavian vein and into the right atrium, using the walls of the superior vena cava for support (block 510). The guide catheter is advanced until the distal tip crosses the tricuspid valve, then torqued 90 degrees counterclockwise to maneuver the distal tip into the same plane as the coronary sinus ostium (block 520). Torque is maintained while pulling the guide catheter back into the right atrium (block 530). An inner catheter is advanced through the guide catheter, beyond the distal tip of the guide catheter, and torqued to locate the coronary sinus ostium (block 540). A guide wire is advanced through the inner catheter and the inner catheter and guide wire are alternately advanced into a side branch of the coronary sinus ostium (block 550). Finally, the guide catheter is advanced over the inner catheter into the side branch of the coronary sinus ostium (block 560).

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

I claim:

1. A guide catheter for cannulating a coronary sinus from a superior vena cava, the guide catheter comprising:

- a flexible elongate shaft having a proximal portion, a middle portion and a distal portion terminating in a distal tip, the distal portion having a preformed shape configured such that the distal portion of the shaft is supported on a wall of the superior vena cava when locating an ostium of the coronary sinus with the distal tip, the preformed shape of the distal portion lying in a single plane and defined at least by:
- a first arc adjacent the middle portion and having a first arc radius ranging from approximately 3 to approximately 4 inches;
- a second arc distally adjacent the first arc and having a second arc radius ranging from approximately 1.2 to approximately 1.8 inches;
- a third arc distally adjacent the second arc and having a third arc radius ranging from approximately 2.2 to approximately 3.7 inches;
- a fourth arc distally adjacent the third arc and having a fourth arc radius ranging from approximately 1 to approximately 1.5 inches; and
- a generally straight terminal portion adjacent the fourth arc and having a length ranging from approximately 0.4 to approximately 1.81 inches.

2. A guide catheter for cannulating a coronary sinus from a superior vena cava, the guide catheter comprising:

- a flexible elongate shaft having a proximal portion and a distal portion terminating in a distal tip, the distal portion having a preformed shape configured such that the distal portion of the shaft is supported on a wall of the superior vena cava when locating an ostium of the coronary sinus with the distal tip, the preformed shape of the distal portion lying in a single plane and having an overall length from approximately 4.2 to approximately 11.81 inches and including at least:
  - a first arc segment having a first arc radius ranging from approximately 3 to approximately 4 inches;
  - a second arc segment having a second arc radius ranging from approximately 1.2 to approximately 1.8 inches;
  - a third arc segment having a third arc radius ranging from approximately 2.2 to approximately 3.7 inches; and a generally straight terminal portion distal to the third arc segment and having a length of up to approximately 1.81 inches.

3. The guide catheter of claim 2, wherein the first arc radius ranges from approximately 3.5 to approximately 4 inches.

4. The guide catheter of claim 3, wherein the first arc radius is approximately 3.88 inches.

5. The guide catheter of claim 2, wherein the first arc segment has a first arc length ranging from approximately 2 to approximately 4 inches.

6. The guide catheter of claim 2, wherein the first arc radius is approximately 3.88 inches and wherein the first arc segment has a first arc length of 3.95 inches.

7. The guide catheter of claim 2, wherein the first arc radius is approximately 3.88 inches and wherein the first arc segment has a first arc length of 3.27 inches.

8. The guide catheter of claim 2, wherein the flexible elongate shaft further includes a deflection location disposed between the proximal portion and the preformed distal portion.

9. The guide catheter of claim 2, wherein a hardness value of a thermoplastic material forming the distal portion decreases from proximally to distally.

10. The guide catheter of claim 2, wherein the first, second and third arc segments are arranged such that the terminal portion is oriented generally parallel to the proximal portion of the shaft.

11. The guide catheter of claim 2, wherein the shaft is configured to slidably receive an inner catheter configured for sub-selecting a branch of the coronary sinus.

12. A guide catheter for cannulating a coronary sinus from a superior vena cava, the guide catheter comprising:

a flexible elongate shaft having a proximal portion and a distal portion terminating in a distal tip, the distal portion having a preformed size and shape configured so that the distal portion of the shaft is supported on a wall of the superior vena cava during insertion of the distal portion into the coronary sinus, the preformed shape of the distal portion lying in a single plane and having an overall length of from approximately 4.2 to approximately 11.81 inches and including at least:

a first arc segment having a first arc radius ranging from approximately 3 to approximately 4 inches;

a second arc segment having a second arc radius ranging from approximately 1.2 to approximately 1.8 inches;

a third arc segment having a third arc radius ranging from approximately 2.2 to approximately 3.7 inches; and a generally straight terminal portion distal to the third arc segment and having a length of up to approximately 1.81 inches.

13. The guide catheter of claim 12, wherein the flexible elongate shaft further includes a deflection location disposed between the proximal portion and the preformed distal portion.

14. The guide catheter of claim 12, wherein a hardness value of a thermoplastic material forming the distal portion decreases from proximally to distally.

15. The guide catheter of claim 12, wherein the first, second and third arc segments are arranged such that the terminal portion is oriented generally parallel to the proximal portion of the shaft.

16. The guide catheter of claim 12, wherein the shaft is configured to slidably receive an inner catheter configured for sub-selecting a branch of the coronary sinus.

* * * * *